United States Patent
Crawford et al.

(10) Patent No.: US 7,468,054 B2
(45) Date of Patent: Dec. 23, 2008

(54) SAFETY SHIELD SYSTEM FOR A SYRINGE

(75) Inventors: Jamie Crawford, New York, NY (US); Frank Francavilla, Branchville, NJ (US); Roger Groskopf, Saddle Brook, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 289 days.

(21) Appl. No.: 10/699,808

(22) Filed: Nov. 3, 2003

(65) Prior Publication Data

US 2005/0096596 A1 May 5, 2005

(51) Int. Cl.
*A61M 5/32* (2006.01)
*A61M 5/00* (2006.01)

(52) U.S. Cl. ........................ 604/198; 604/110

(58) Field of Classification Search ......... 604/192–198, 604/263, 110
See application file for complete search history.

(56) References Cited

U.S. PATENT DOCUMENTS

| | | |
|---|---|---|
| 4,573,976 A | 3/1986 | Sampson |
| 4,631,057 A | 12/1986 | Mitchell |
| 4,737,144 A | 4/1988 | Choksi |
| 4,747,831 A | 5/1988 | Kulli |
| 4,795,432 A | 1/1989 | Karczmer |
| 4,813,940 A | 3/1989 | Parry |
| 4,985,021 A | 1/1991 | Straw |
| 4,998,920 A | 3/1991 | Johnson |
| 5,026,356 A | 6/1991 | Smith |
| 5,053,018 A | 10/1991 | Talonn |
| 5,061,251 A | 10/1991 | Juhasz |
| 5,151,088 A | 9/1992 | Allison |
| 5,156,599 A | 10/1992 | Ranford |
| 5,163,918 A | 11/1992 | Righi |
| 5,193,552 A | 3/1993 | Columbus |
| 5,197,953 A | 3/1993 | Colonna |
| 5,201,708 A | 4/1993 | Martin |
| 5,217,437 A | 6/1993 | Talonn |
| 5,242,420 A | 9/1993 | Martin |

(Continued)

FOREIGN PATENT DOCUMENTS

EP    0 307 367 A1    6/1992

(Continued)

*Primary Examiner*—Kevin C. Sirmons
*Assistant Examiner*—Andrew M Gilbert
(74) *Attorney, Agent, or Firm*—David M. Fortunato; Cohen, Pontani, Lieberman & Pavane LLP

(57) ABSTRACT

A medical device for delivering medicament to a patient including a syringe assembly, a shield body, a retainer and an urging member. The syringe assembly includes a barrel defining a reservoir for medicament, a needle cannula coupled to the barrel and in fluid communication with the reservoir, a plunger having a stopper positioned in the reservoir and a thumb pad for moving the plunger in the reservoir. The syringe barrel is movable within the shield body between a first position exposing the forward tip of the needle cannula, and a second position where the tip of the needle cannula is in the shield body. A retainer secures the syringe barrel in the first position. An urging member urges the syringe barrel from the first position toward the second position upon interaction with the thumb pad and upon the release of pressure applied to the thumb pad.

24 Claims, 8 Drawing Sheets

U.S. PATENT DOCUMENTS

| | | | |
|---|---|---|---|
| 5,246,427 A | 9/1993 | Sturman | |
| 5,267,976 A * | 12/1993 | Guerineau et al. | 604/198 |
| 5,273,541 A | 12/1993 | Malenchek | |
| 5,300,040 A | 4/1994 | Martin | |
| 5,304,149 A | 4/1994 | Morigi | |
| 5,308,332 A | 5/1994 | Dilllard, III | |
| 5,312,372 A | 5/1994 | DeHarde et al. | |
| 5,336,176 A | 8/1994 | Yoon | |
| 5,342,309 A | 8/1994 | Hausser | |
| 5,342,320 A | 8/1994 | Cameron | |
| 5,370,628 A | 12/1994 | Allison | |
| 5,385,555 A | 1/1995 | Hausser | |
| 5,389,085 A | 2/1995 | D'Alessio | |
| 5,417,660 A | 5/1995 | Martin | |
| 5,562,626 A | 10/1996 | Sanpietro | |
| 5,651,774 A | 7/1997 | Taranto | |
| 5,658,254 A | 8/1997 | Reichenbach | |
| 5,681,292 A | 10/1997 | Tober | |
| 5,713,871 A | 2/1998 | Stock | |
| 5,735,823 A | 4/1998 | Berger | |
| 5,769,822 A | 6/1998 | McGary | |
| 5,800,395 A | 9/1998 | Botich | |
| 5,800,403 A | 9/1998 | Pressly | |
| 5,882,342 A | 3/1999 | Cooper | |
| 6,017,329 A | 1/2000 | Hake | |
| 6,077,253 A | 6/2000 | Cosme | |
| 6,162,197 A | 12/2000 | Mohammad | |
| 6,186,980 B1 * | 2/2001 | Brunel | 604/110 |
| 6,206,853 B1 * | 3/2001 | Bonnet | 604/110 |
| 6,228,054 B1 | 5/2001 | Dysarz | |
| 6,319,233 B1 | 11/2001 | Jansen | |
| 6,432,087 B1 | 8/2002 | Hoeck et al. | |
| 6,432,088 B1 | 8/2002 | Huang et al. | |
| 6,440,104 B1 | 8/2002 | Newby et al. | |
| 6,443,929 B1 | 9/2002 | Kuracina | |
| 6,458,101 B1 | 10/2002 | Hu | |
| 6,458,105 B1 | 10/2002 | Rippstein et al. | |
| 6,461,333 B1 | 10/2002 | Frezza | |
| 6,461,362 B1 | 10/2002 | Halseth | |
| 6,475,194 B2 | 11/2002 | Domici, Jr. | |
| 6,478,780 B1 | 11/2002 | Shields | |
| 6,494,863 B1 | 12/2002 | Shaw | |
| 6,511,460 B1 | 1/2003 | Arnissolle | |
| 6,514,229 B1 | 2/2003 | Huang | |
| 6,527,742 B1 | 3/2003 | Malenchek | |
| 6,530,903 B2 | 3/2003 | Wang | |
| 6,547,762 B1 | 4/2003 | Botich et al. | |
| 6,558,357 B1 | 5/2003 | Hoeck | |
| 6,565,540 B1 | 5/2003 | Perouse | |
| 6,569,115 B1 | 5/2003 | Barker | |
| 6,569,124 B1 | 5/2003 | Perouse | |
| 6,585,702 B1 | 7/2003 | Brunel | |
| 6,589,209 B1 | 7/2003 | Dysarz | |
| 6,595,954 B1 | 7/2003 | Luther | |
| 6,605,073 B1 | 8/2003 | Pressly | |
| 6,613,022 B1 | 9/2003 | Doyle | |
| 6,623,459 B1 * | 9/2003 | Doyle | 604/197 |
| 6,918,889 B1 * | 7/2005 | Brunel | 604/110 |
| 6,966,898 B1 * | 11/2005 | Pouget et al. | 604/197 |
| 2002/0065488 A1 | 5/2002 | Suzuki et al. | |
| 2002/0193737 A1 | 12/2002 | Popovsky | |
| 2002/0193746 A1 | 12/2002 | Chevallier | |
| 2002/0193747 A1 | 12/2002 | Denolly | |
| 2003/0023205 A1 | 1/2003 | Botich | |
| 2003/0028171 A1 | 2/2003 | DeHarade | |
| 2003/0036730 A1 | 2/2003 | Von Teichert | |
| 2003/0050601 A1 | 3/2003 | Righi | |
| 2003/0050607 A1 | 3/2003 | Gaagnieux | |
| 2003/0078546 A1 | 4/2003 | Jensen | |
| 2003/0083627 A1 | 5/2003 | Chen | |
| 2003/0114799 A1 | 6/2003 | Cheikh | |
| 2003/0144630 A1 | 7/2003 | Chang | |
| 2003/0149403 A1 | 8/2003 | Barker | |
| 2003/0149404 A1 | 8/2003 | Lehmann | |

FOREIGN PATENT DOCUMENTS

| | | |
|---|---|---|
| EP | 0 680 767 A1 | 11/1995 |
| EP | 0 864 335 A2 | 9/1996 |
| EP | 0 740 942 A1 | 11/1996 |
| EP | 0 966 983 A1 | 12/1999 |
| EP | 1 258 263 A1 | 11/2002 |
| EP | 1 260 242 A1 | 11/2002 |
| EP | 0 901 391 B1 | 1/2003 |
| EP | 0 963 213 B1 | 1/2003 |
| EP | 1 273 316 A1 | 1/2003 |
| EP | 1 281 410 A1 | 2/2003 |
| EP | 0 916 354 B1 | 3/2003 |
| EP | 1 287 842 A1 | 3/2003 |
| EP | 1 291 029 A1 | 3/2003 |
| EP | 1 291 030 A1 | 3/2003 |
| EP | 1 317 938 A1 | 6/2003 |
| EP | 0 984 804 B1 | 7/2003 |
| EP | 1 329 234 A2 | 7/2003 |
| EP | 0 941 134 B1 | 8/2003 |
| EP | 1 205 173 A2 | 9/2003 |
| EP | 1 205 173 A3 | 9/2003 |
| EP | 0 734 738 B1 | 10/2003 |
| EP | 1 049 503 B1 | 10/2003 |
| FR | 2 830 764 A1 | 4/2003 |
| FR | 2 830 765 A1 | 4/2003 |
| GB | 2 282 069 A | 3/1995 |
| JP | 2001193714 | 12/2002 |
| WO | WO 01/41841 A2 | 6/2001 |
| WO | WO 01/41841 A3 | 6/2001 |
| WO | WO 01/60435 A1 | 8/2001 |
| WO | WO 01/85238 A2 | 11/2001 |
| WO | WO 02/089878 A1 | 11/2002 |
| WO | WO 02/098480 A2 | 12/2002 |
| WO | WO 02/098494 A2 | 12/2002 |
| WO | WO 02/098494 A3 | 12/2002 |
| WO | WO 03/000322 A1 | 1/2003 |
| WO | WO 03/000323 A1 | 1/2003 |
| WO | WO 03/011378 A1 | 2/2003 |
| WO | WO 03/015852 A1 | 2/2003 |
| WO | WO 03/022335 A2 | 3/2003 |
| WO | WO 03/033059 A1 | 4/2003 |
| WO | WO 03/033060 A1 | 4/2003 |
| WO | WO 03/041766 A2 | 5/2003 |
| WO | WO 03/045476 A1 | 6/2003 |
| WO | WO 03/045480 A1 | 6/2003 |
| WO | WO 03/045481 A1 | 6/2003 |
| WO | WO 03/063934 A1 | 8/2003 |
| WO | WO 03/068297 A1 | 8/2003 |
| WO | WO 03/068298 A1 | 8/2003 |

* cited by examiner

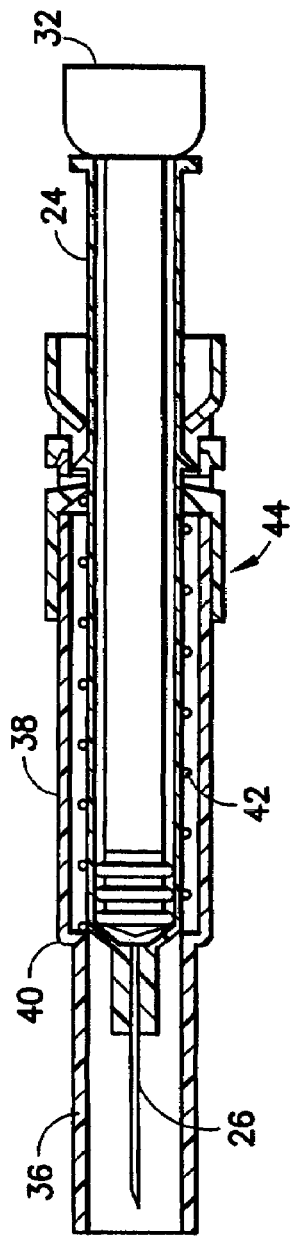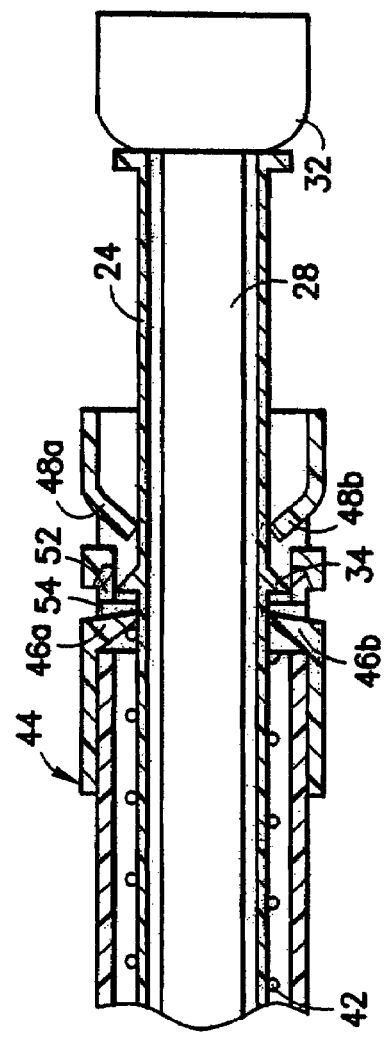

SAFETY SHIELD SYSTEM FOR A SYRINGE

BACKGROUND OF THE INVENTION

1. Field of the Invention

The present invention relates to a prefilled medical device for delivering a dose of medicament by injection and having an integral shield system for preventing accidental needle sticks after use. More particularly, the present invention is directed to a syringe assembly including a safety shield system.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled medicament. Such syringes typically include a cylindrical hollow barrel which may be formed of a glass or plastic material and which includes the medicament. One end of the barrel is fitted with a fixed or removable hollow needle, and the other end of the barrel receives a plunger having a stopper which is slidable with respect to the barrel for delivery of the medicament to the hollow needle, i.e., to urge the medicament toward and out of the needle. A syringe assembly, which typically includes the above-described components, is usually stored with a removable needle cover which protects the needle from damage during storage and handling. Prior to use, the needle cover is removed to expose the needle.

To prevent a syringe user and, in particular, a health care professional from inadvertent sticks by the needle after use of the syringe on a patient, the syringe assembly may incorporate a safety shield which forms a guard to cover the needle after use, such as by telescopingly extending the shield from the syringe body over the needle. Some such shields are spring activated for imparting a telescoping-like deployment action to the safety shield. Certain attributes to be considered in such syringe assemblies are that the shield should be intuitive and easy to use, should preferably provide consistent and reliable shield deployment, and should be operable with one hand. Other attributes are that such syringe assemblies require no change in current medicament delivery techniques, allow for dose adjustment, are preferably autoclavable, and allow for the inspection of contents before and after activation of the shield. Moreover, the use of the shield must not detrimentally affect processing and filling of the syringe at the pharmaceutical company, the assembly (i.e., syringe assembly and safety shield) must be easy to manufacture, must prevent accidental activation, and must limit the possibility of incurring cosmetic or structural damages.

SUMMARY OF THE INVENTION

The present invention relates to a syringe assembly incorporating a safety shield for covering the needle of the syringe assembly after administration of a dosage of medicament. The safety shield is automatically activated upon full delivery of the medicament dosage in the syringe.

According to the present invention, a syringe assembly medical device for delivering a medicament to a patient includes a syringe having a syringe barrel defining a reservoir within which a medicament may be held; the syringe barrel having a front end and a rear end. A needle or needle cannula (those terms being used interchangeably herein) is provided proximate the front end of the barrel and is in fluid communication with the reservoir. The syringe barrel is disposed in a hollow shield body. A first retainer prevents rearward motion of the syringe barrel relative to the hollow shield body when the syringe barrel has been fully inserted in the shield body to an operative position. An urging member is arranged between a portion of the hollow shield body and a portion of the syringe barrel for urging the syringe barrel rearward when the syringe barrel is in the operative position. The urging member may be, by way of non-limiting example, a coil spring. The syringe barrel is movable between a first position, in which a forward tip of the needle cannula is exposed, and a second position, in which the syringe barrel is fully retracted in the shield body and the forward tip of the needle cannula is contained within the shield body to prevent the tip of a finger from contacting the needle tip.

The syringe assembly includes a plunger having a first end with a stopper inserted in the syringe barrel. The second end of the plunger has a thumb pad or thumb press area for receiving medicament delivery pressure for pressing the plunger into the syringe barrel to deliver the medicament. The terms "thumb pad" and "thumb press area" are used interchangeably herein and designate a region coupled to or otherwise formed on an end of the plunger and which may be depressed by the thumb or finger of a user during use of the medical device. The thumb pad is designed to engage a release mechanism for releasing the first retainer after the stopper has reached a first retainer release position in the barrel, i.e. corresponding to a position at which the dose of medicament contained within the reservoir has been fully delivered. After the first retainer has been released and after removal or sufficient reduction of medicament delivery pressure from the thumb pad, the urging member provides a force for moving the syringe barrel rearward toward a fully retracted position in which the entire needle cannula is located within, and protected by, the hollow shield body.

The medical device may include a flange clip connected at a rear end of the shield body. The first retainer is arranged on the flange clip and the flange clip is placed about the shield body after the syringe barrel has been inserted into the shield body.

The syringe barrel may further comprise a radial flange arranged on an outer circumference of the syringe barrel between the front and rear ends thereof. The urging member may be arranged between the flange and a rearward facing step in the shield body. The flange clip may further include a second retainer which is used when the syringe barrel is moved to its fully retracted position. In that position, a forward facing portion of the syringe barrel flange is blocked from moving forward by the second retainer.

The first and second retainers may be formed separately from, or unitarily with the shield body. For unitarily formed retainers, the first and/or second retainers are required to be held in a non-blocking position while the syringe barrel is inserted into the shield body. Of course, it may be possible to manufacture the shield body such that the retainers are held in a non-blocked position until insertion of the syringe barrel, which causes the retainers to move to their operative positions.

A step may be formed in the shield body to divide the shield body into a forward cylindrical section and a rearward cylindrical section, with a diameter of the rearward cylindrical section being different and preferably larger than a diameter of the forward cylindrical section.

In an alternative embodiment, the urging member is a spring which may be arranged between the rearward facing step in the shield body and a front face of the syringe barrel. In this latter embodiment, the spring does not hinder the view of the contents of the syringe barrel.

In a further alternative embodiment, the syringe barrel includes two flanges on an outer circumference thereof. When the syringe barrel is moved to the fully retracted position, the first retainer is arranged between the two flanges, thereby preventing both forward and rearward movement of the syringe barrel relative to the shield body.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 11 is a cross-sectional view of the device of FIG. 2 with the shield body deployed in a safety position after use;

FIG. 12 is an enlarged cross-sectional view of the flange clip and syringe barrel in the position shown in FIG. 11;

DETAILED DESCRIPTION OF THE PREFERRED EMBODIMENTS

Figure 1:
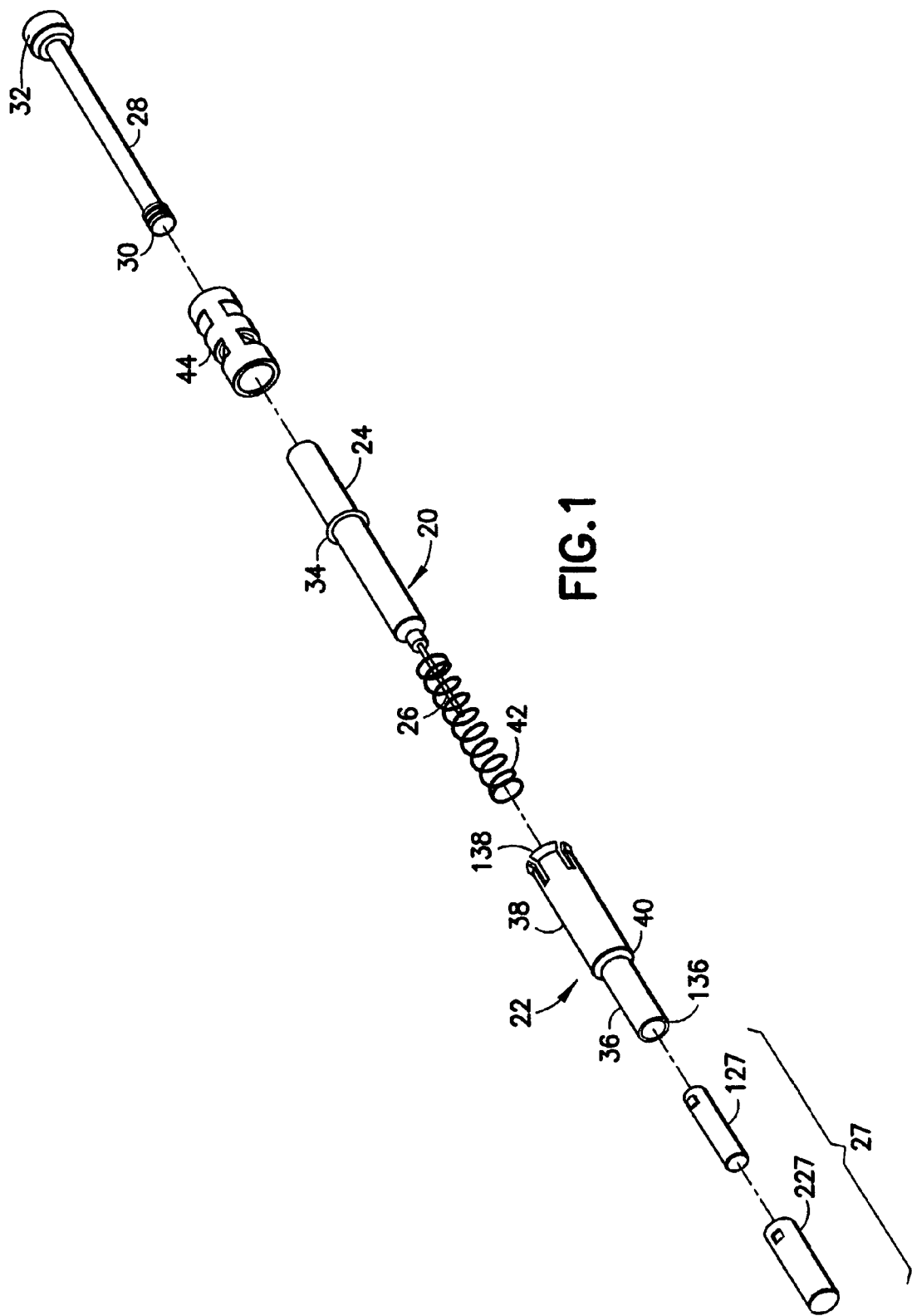
FIG. 1 is an exploded perspective view of the components of a medical device according to an embodiment of the present invention.
Figure 2:
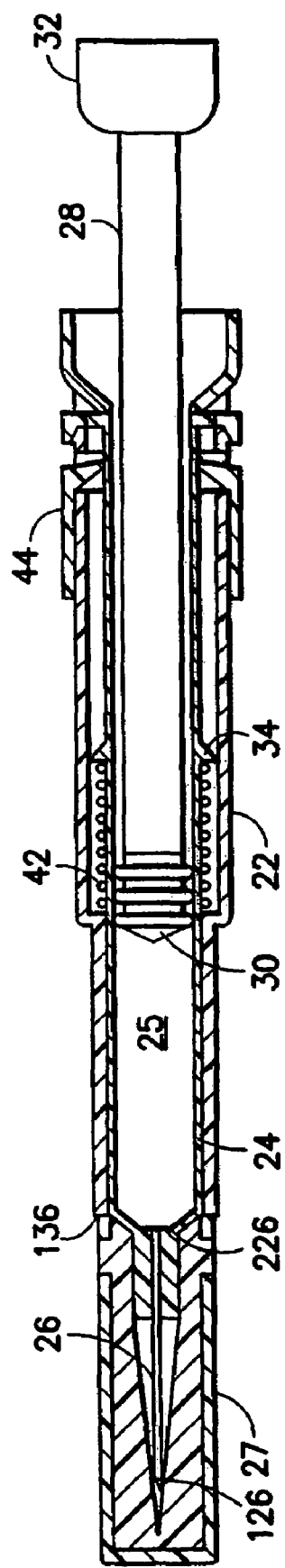
FIG. 2 is a cross-sectional view of the assembled medical device of FIG. 1 prior to use.

FIGS. 1 and 2 show a medical device 10 for delivery of a medicament into a patient constructed in accordance with an embodiment of the present invention. As used herein, the term "medicament" is intended to refer to any drug substance, vaccine, or other liquid substance that is injected into a patient. The medical device 10 includes a syringe assembly 20 which can be prefilled with the medicament to be delivered, and a shield body 22 which surrounds a portion of the syringe 20.

The syringe assembly 20 includes a cylindrical barrel 24 defining a reservoir 25 within which the medicament may be held prior to use of the medical device 10. The syringe assembly 20 also includes a needle cannula 26 having a forward tip 126 and a rearward end 226 in fluid communication with the reservoir 25. The needle cannula 26 may be permanently connected to a front end of the barrel 24 using an adhesive, glue, interference fit or other known or hereafter developed material or technique, or it may be detachable from the barrel 24 such as, for example, using a luer-type connection. The barrel 24 also includes a radial flange 34 arranged between the ends of the barrel 24 which interacts with the shield body 22 as explained in detail below. To incorporate the radial flange 34 into/onto the barrel 24, the barrel 24 is preferably made of a molded plastic. Alternatively, the barrel 24 may be formed from glass. A plunger rod 28 (see also FIG. 3) has a first end inserted in the barrel 24 with a stopper or piston 30 arranged on the first end that is movable with the plunger rod 28 within the barrel 24. A second end of the plunger rod 28 includes a thumb pad 32 used for receiving pressure from the user's thumb for moving the piston 30 into and within the barrel 24. As further shown in FIGS. 1 and 2, a removable needle shield 27 is disposed over the needle cannula 26 on the front end of the barrel 24 to protect the needle from damage during handling of the syringe assembly, and to protect users from being stuck by the needle prior to its intended use. The needle shield 27 preferably includes a pliable part 127 and a rigid part 227.

The syringe barrel 24 may be caused to move between a first position, in which the forward tip 126 of the needle cannula 26 extends beyond a first free end 136 of the shield body 22 (described below), and a second position in which the syringe barrel 24 is fully retracted within the shield body 22 and the forward tip 126 of the needle cannula 26 is contained within the shield body 22.

Figure 4:
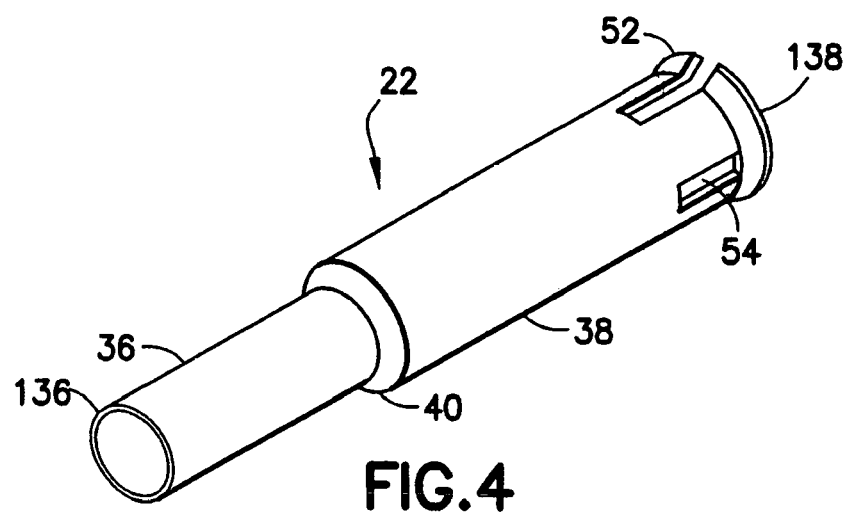
FIG. 4 is a perspective view of a shield body of the medical device shown in FIG. 1.

The various component parts of the inventive medical device 10 will now be discussed in further detail. The shield body 22 is depicted in FIG. 4 and includes a first or forward cylindrical portion 36 having a first free end 136 and a second or rearward cylindrical portion 38 having a second free end 138. The first cylindrical portion 36 has a smaller diameter than the second cylindrical portion 38 so that a step 40 is formed therebetween. As shown in FIG. 2, the front end of the barrel 24 is contained within the shield body 22 so that the forward tip 126 of the needle cannula 26 is positioned beyond the first free end 136 of the first cylindrical portion 36 when the syringe barrel 24 is positioned in the first position (see, e.g., FIG. 7). The inner diameter of the first cylindrical portion 36 is slightly larger than the outer diameter of the barrel 24 such that the barrel 24 is axially movable within the shield body 22 with interference between the barrel 24 and first cylindrical portion 36. The shield body 22 is preferably molded from transparent plastic so that the medicament contained within the reservoir 25 may be viewed by the pharmaceutical company during the filling process and by the health care professional prior to and during use of the inventive medical device 10. A partial list of materials which may be used to form the shield body include acrylic, PET, polystyrene, polypropylene or polycarbonate materials. Of course, it is desirable that any material used be transparent so that the contents of the barrel 24 may be viewed. Also, although the shield body 22 is shown as including solid cylindrical portions, vent holes may be incorporated therein to allow the escape of moisture which may become trapped between the shield body 22 and the barrel 24 as a result of an autoclave or other sterilization process. Moreover, windows may be cut or otherwise formed into the shield body 22 to allow for easier inspection of the syringe contents.

Referring back to FIGS. 1 and 2, an urging member 42, such as, for example, a coil spring or biasing arm, is positioned over the front end of the barrel 24 so that one end of the spring 42 rests against the radial flange 34 and the other end of the spring 42 is seated within the second cylindrical portion 38 of the shield body 22 and against the step 40. The spring 42 is charged in the assembled state of the device 10 shown in FIG. 2 and biases the syringe barrel 24 toward the second position in which the syringe barrel 24 is retracted into the shield body 22. The length and/or position of the spring 42 may be adjusted to increase or decrease the visible area of the barrel 24. As explained below, to maintain the barrel 24 against the spring 42 so that the spring remains charged when the medical device 10 is in its pre-use state (see, e.g., FIG. 2), a flange clip 44 is attached to the second free end 138 of the second cylindrical portion 38 of the shield body 22.

Figure 5:
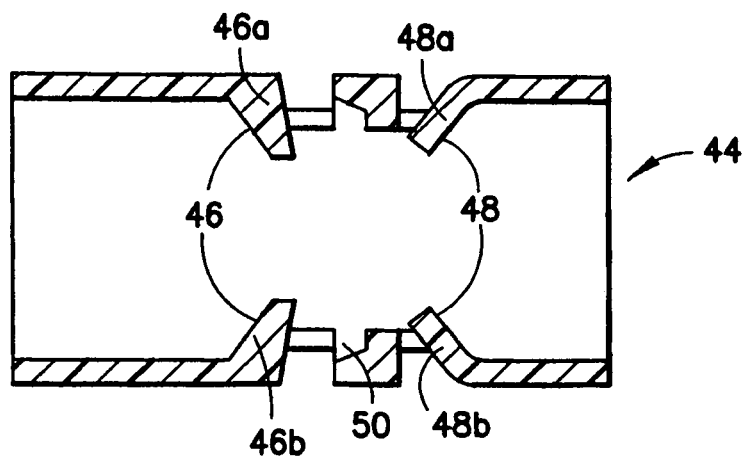
FIG. 5 is a longitudinal sectional view of a flange clip of the medical device shown in FIG. 1.
Figure 6:
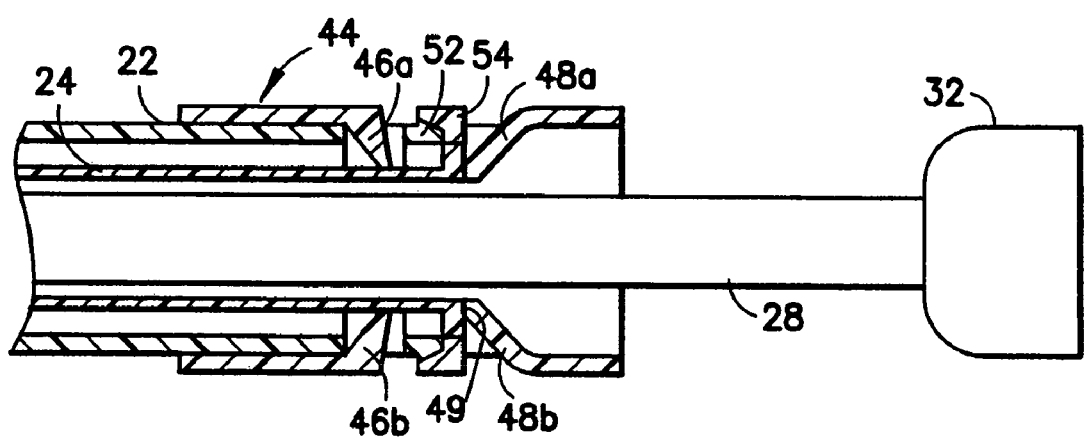
FIG. 6 is an enlarged view of the interaction between the shield body, the barrel and the flange clip of the medical device shown in FIG. 2.

Referring to FIGS. 5 and 6, the flange clip 44 has forward flexing arms 46a, 46b (collectively referred to as forward flexing arms 46) and rear flexing arms 48a, 48b (collectively referred to as rear flexing arms 48). Although two forward flexing arms 46 and two rear flexing arms 48 are shown, one or more of each of the flexing arms may be used to achieve the desired results described in detail below. An annular recess 50 is defined in the inner surface of the flange clip 44 between the forward and rear flexing arms 46, 48. This annular recess 50 receives a radial rim 52 arranged proximate the free end of the second cylindrical portion 38 on the shield body 22 as the flange clip 44 is inserted over the free end of the second cylindrical portion 38. Once the radial rim 52 is received in the annular recess 50, the flange clip 44 is held in place on the shield body 22 and the barrel 24 is held within the shield body 22 in the position shown in FIG. 2 against the urgency of the spring 42 by the rear flexing arms 48. Accordingly, the rear flexing arms 48 also function as retainers. FIG. 6 is an enlarged view of the interaction between the shield body 22, the flange clip 44 and the rear end of the barrel 24. As shown, the rear end of the barrel 24 is urged against axially forward facing surfaces of the rear flexing arms 48 in this state. The rear end of the barrel 24 may be flanged or otherwise suitably sized and shaped for this purpose. Furthermore, a portion of the forward flexing arms 46 extend through windows 54 in the shield body 22 in this state. The purpose of the forward flexing arms 46 is explained below.

Figure 7:
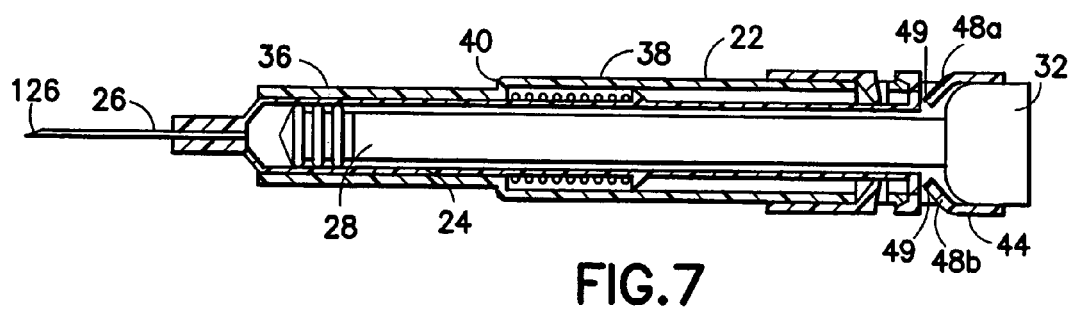
FIG. 7 is a cross-sectional view of the device of FIG. 2 after a partial delivery of a dosage in the medical device.

FIG. 7 shows the medical device 10 during use, with the syringe barrel 24 deployed in the first position. In this state, the needle shield 27 (see FIG. 2) has been removed, the forward tip 126 of the needle cannula 26 is fully exposed, and the plunger 28 has been pushed into the barrel 24 such that a majority of the contents of the barrel 24 has been delivered. The flange clip 44, barrel 24 and shield body 22 are in the same relative positions in this state as in the state shown in FIG. 2.

Figure 8:
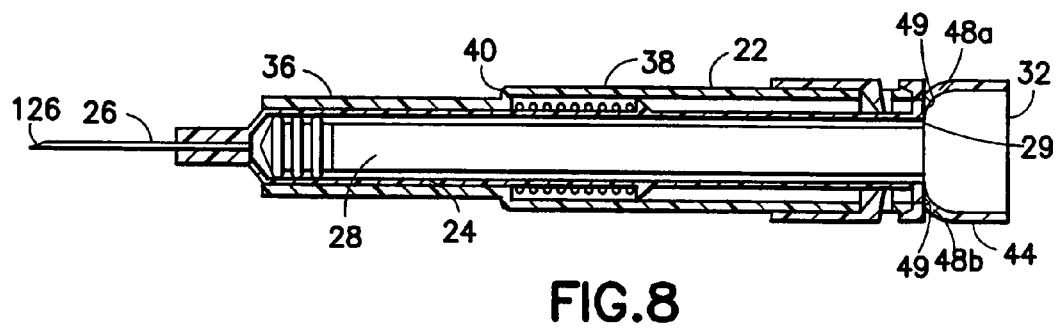
FIG. 8 is a cross-sectional view of the device of FIG. 2 after a full delivery of a dosage in the medical device.
Figure 9:
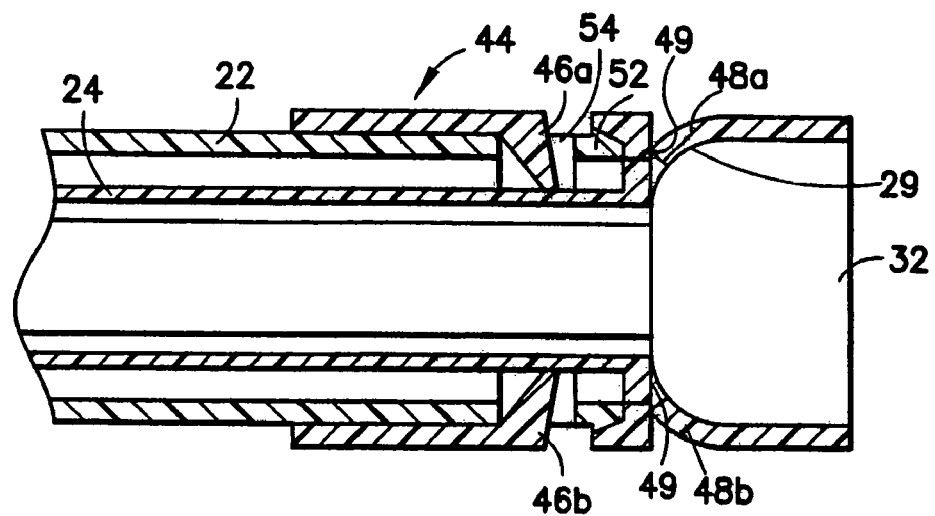
FIG. 9 is an enlarged view of the flange clip in the position shown in FIG. 8.

FIG. 8 shows the medical device 10 after the plunger has been fully depressed into the barrel 24. In this state the thumb pad 32 contacts the rear flexing arms 48 of the flange clip 44 and forces them to move radially outward relative to each other and the rear end of the barrel 24 no longer abuts the front facing portions 49 of the rear flexing arms 48. The urgency of the spring 42 moves the rear end of the barrel 24 against the front facing surface 29 of the thumb pad 32. FIG. 9 is an enlarged view of the interaction between the thumb pad 32, the flange clip 44, and the barrel 24 in this state.

Figure 3:
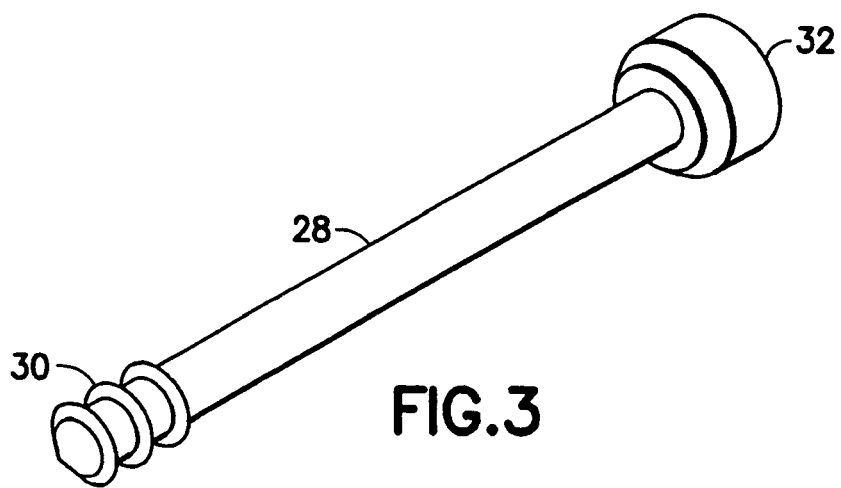
FIG. 3 is a perspective view of a plunger rod of the medical device shown in FIG. 1.
Figure 10:
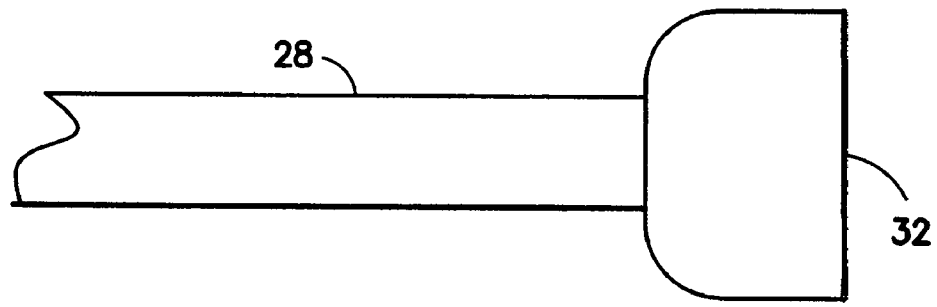
FIG. 10 is a side view of an alternative embodiment of a thumb pad of the medical device of the present invention.
Figure 10A:
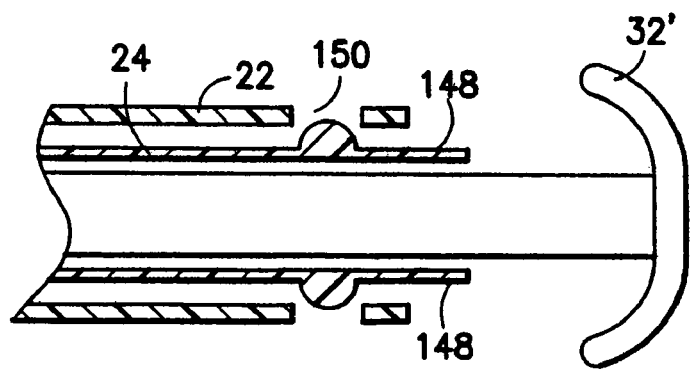
FIG. 10a is a partial cross-sectional view of a further embodiment of the thumb pad and retaining arms of the medical device of the present invention.

To accomplish the desired interaction between the thumb pad 32 and flange clip 44, i.e., release of rear flexing arms 48 to enable movement of the syringe barrel 24 from the first position to the second position, the front facing surface 29 of the thumb pad 32 may be conically-shaped as shown in FIGS. 1, 2, and 3. Alternatively, the front facing surface 29 of the thumb pad 32 may be configured as shown in FIG. 10a. Of course, any shape may be used as long is it has the desired effect of flexing the rear flexing arms 48 radially outward to the extent necessary to release the barrel 24 from flange clip 44.

Alternatively, the thumb pad 32' may be configured as a mushroom-shaped head having a rim which overlaps a portion of the rear flexing arms 148 to urge the flexing arms radially inward toward each other. In this embodiment, which is shown in FIG. 10a, the rear retaining arms are designated as arms 148 and may be arranged on or connected to the barrel 24. As shown, the arms 148 engage a recess 150 arranged on or connected to the shield body 22.

After the rear flexing arms 48 have been displaced, the plunger 28 may be released by the operator of the medical device 10 and the syringe barrel 24 may move freely from the first position to the second position. This diminishes or removes the pressure applied to thumb pad 32. Thereafter the barrel 24 with the needle cannula 26 attached thereto will be caused by the spring 42 to retract into the shield body 22 until the radial flange 34 of the barrel 24 moves into a resting position between the forward and rear flexing arms 46, 48 as shown in FIG. 11. Specifically, as the barrel 24 retracts, it follows the movement of the plunger and the radial flange 34 passes the forward flexing arms 46 and urges them radially outward from each other. As shown in FIG. 5, the front facing surfaces 56 of the forward flexing arms 46 are inclined with respect to each other and the rear facing surface 58 of the radial flange 34 are inclined with respect to each other so that the forward flexing arms 46 slide over the radial flange 34 and move radially outward when the radial flange passes the forward flexing arms. However, the interaction between the radial flange 34 and the rear flexing arms 48 is such that the rear flexing arms are not forced radially outward by the radial flange, thereby locking radial flange 34 into position between arms 46, 48. This position corresponds to a fully retracted state of the barrel 24 so that the needle cannula 26 is fully received in the shield body 22 and the forward tip 126 of the needle cannula 26 is protected by the shield body 22. The barrel 24 is thereafter prevented from moving forward because the rear facing surface of the forward flexing arms 46 and the front facing surface of the radial flange 34 are not inclined.

Figure 13:
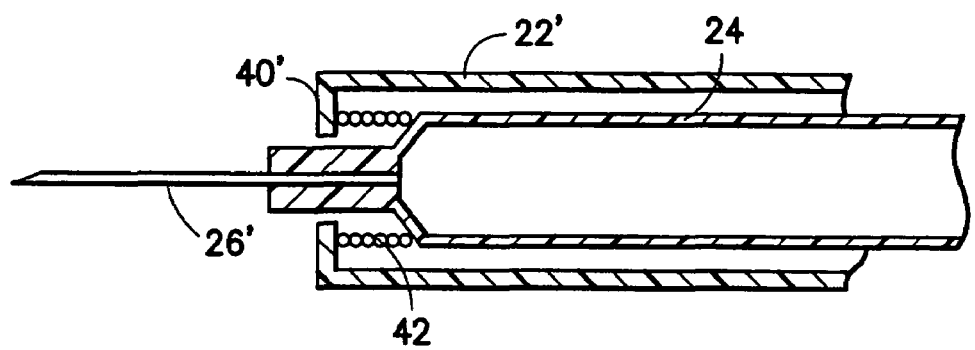
FIG. 13 is a cross-sectional view of an embodiment in which the urging member is arranged against a front face of a syringe barrel.

FIG. 13 shows an alternative embodiment in which the urging member 42 is arranged between a step 40' proximate a front end of a shield body 22' and a front face of the barrel 24. This embodiment allows the entire dosage of medicament to be viewed because the urging member 42 is arranged in front of the barrel 24. In this embodiment, the flange 34 (not shown in FIG. 13) is used only to retain the barrel in the fully retracted position. However, a longer needle cannula 26' relative to the needle cannula 26 in the previously-discussed embodiments may be required to provide proper clearance of the front of the shield body 22'.

Figure 14:
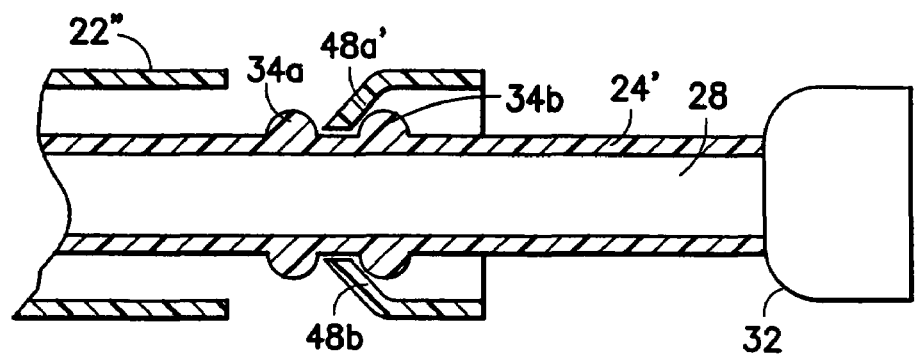
FIG. 14 is a cross-sectional view of an embodiment having two flanges on a syringe barrel.

FIG. 14 shows yet a further embodiment in which the barrel 24' includes two radial flanges 34a, 34b. In this embodiment, only one pair of flexing arms 48a', 48b' is required. This embodiment also shows that the flexing arms 48a', 48b' are formed as one piece with the shield body 22". When the barrel 24' is moved to the fully retracted position in this embodiment, the spring 42 is designed to push the barrel 24' to a position in which only one of the radial flanges 34b passes the flexing arms 48a', 48b'. Accordingly, the flexing arms 48a',

48b' block movement of the barrel 24' in both the forward and rearward movements relative to the shield body 22". As in the embodiments described above, one or more flexing arms 48' may be used.

A description of an exemplary usage of the medical device 10 of the present invention will now be provided. It should be understood by a person of ordinary skill in the art that the following description is provided as an illustrative and non-limiting example. The health care professional receives the inventive medical device 10 prefilled with a desired single dosage of a medicament. Immediately prior to use, the needle shield 27 is removed and the needle cannula 26 and forward tip 126 are exposed. The health care professional pierces the patient's skin with the forward tip 126 of the needle cannula 26 and depresses the thumb pad 32 to cause the plunger rod 28 and piston 30 to move within the reservoir 25. As the plunger rod 28 and piston are caused to move into the reservoir 25, the medicament is caused to be expelled from the reservoir, through the needle cannula 24, and into the patient. When the medicament is completely expelled from the reservoir (i.e., the dose has been completely administered), the thumb pad 32 interacts with the flange clip 44, as described in detail above, thereby releasing the syringe barrel 24 and enabling the syringe barrel 24 to move from the first position to the second position under the force of the spring or urging member 42. When in the second position, the forward tip 126 of the needle cannula 24 will be completely contained within the shield body 22, thus preventing undesired and inadvertent exposure of the health care professional to the contaminated forward tip 126. The used medical device 10 may then be disposed of in a suitable sharps disposal container.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical device for delivering a medicament to a patient, comprising:
   a syringe assembly comprising:
      a barrel having a forward end and a rear end and defining a reservoir within which the medicament may be contained, said barrel having a radial flange arranged between said forward end and said rear end;
      a needle cannula having a forward tip and being coupled to said forward end of said barrel and in fluid communication with said reservoir; and
      a plunger having a first end with a stopper positioned in said reservoir and a second end having a thumb pad for receiving medicament delivery pressure for causing said plunger to move within said reservoir to cause the medicament to be expelled from said reservoir;
   a hollow shield body receiving said syringe barrel therein, said syringe barrel being selectively movable within said shield body between a first position in which said forward tip of said needle cannula is exposed, and a second position in which said forward tip of said needle cannula is contained within said shield body;
   a flange clip fixedly coupled to said hollow shield body proximate a rear facing end of said hollow shield body, wherein said flange clip comprises a first retainer fixedly coupled to said hollow shield body to prevent axial movement of said first retainer with respect to said hollow shield body, said first retainer releasably securing said syringe barrel in said first position, and a second retainer spaced axially from said first retainer, wherein said radial flange is positioned between said first and second retainers when said syringe barrel is in said second position, said hollow shield body further comprises a rim and said flange clip comprises a recess engaging said rim for connecting said flange clip to said hollow shield body, said recess being arranged axially between said first and second retainers; and
   an urging member acting on a portion of said hollow shield body and said radial flange of said syringe barrel for urging said syringe barrel from said first position toward said second position, said thumb pad being configured to interact with said first retainer upon movement of said stopper to a position proximate said syringe barrel forward end to release said syringe barrel from said first retainer and enable said urging member to move said syringe barrel from said first position to said second position upon release of medicament delivery pressure from said thumb pad.

2. The medical device of claim 1, wherein said hollow shield body further comprises a step having a rear facing surface for receiving an end of said urging member.

3. The medical device of claim 2, wherein said step divides said hollow shield body into a first cylindrical portion having a first diameter and a second cylindrical portion having a second diameter different than said first diameter, said urging member being arranged in said second cylindrical portion.

4. The medical device of claim 1, wherein a front facing surface of said second retainer and a rear facing surface of said radial flange are mutually inclined to allow said flange to pass over said second retainer when said syringe barrel is moved from said first position toward said second position.

5. The medical device of claim 1, wherein said first and second retainers comprise flexible arms.

6. The medical device of claim 1, wherein said urging member comprises a spring.

7. The medical device of claim. 1, wherein said first retainer is formed unitarily with said shield body.

8. The medical device of claim 1, wherein said syringe barrel is plastic.

9. The medical device of claim 6, wherein said shield body comprises a step having a rear facing surface for receiving an end of said spring.

10. The medical device of claim 9, wherein said syringe barrel further comprises a radial flange for receiving another end of said spring.

11. The medical device of claim 10, wherein said step divides said hollow shield body into a first cylindrical portion having a first diameter and a second cylindrical portion having a second diameter different than said first diameter, said spring being arranged in said second cylindrical portion.

12. The medical device of claim 1, wherein said first retainer is moved radially outward to release said syringe barrel.

13. A combination comprising a medical syringe assembly and a safety shield, said medical syringe assembly comprising a barrel having a forward end and a rear end and defining a reservoir within which a medicament may be contained, said barrel having a radial flange arranged between said forward end and said rear end, a needle cannula having a forward tip and being coupled to said forward end of said barrel and in fluid communication with said reservoir, and a plunger having a first end with a stopper positioned in said reservoir and a second end having a thumb pad for receiving medicament delivery pressure for causing said plunger to move within said reservoir to cause the medicament to be expelled from said reservoir;

said safety shield comprising a hollow shield body receiving said syringe barrel therein, said syringe barrel being selectively movable within said shield body between a first position in which said forward tip of said needle cannula is exposed, and a second position in which said forward tip of said needle cannula is contained within said shield body, and a flange clip fixedly coupled to said hollow shield body proximate a rear facing end of said hollow shield body, wherein said flange clip comprises a first retainer fixedly coupled to said hollow shield body to prevent axial movement of said first retainer with respect to said hollow shield body, said first retainer releasably securing said syringe barrel in said first position, and a second retainer spaced axially from said first retainer, wherein said radial flange is positioned between said first and second retainers when said syringe barrel is in said second position, said hollow shield body further comprises a rim and said flange clip comprises a recess engaging said rim for connecting said flange clip to said hollow shield body, said recess being arranged axially between said first and second retainers; and an urging member acting on a portion of said hollow shield body and said radial flange of said syringe barrel for urging said syringe barrel from said first position toward said second position, said thumb pad being configured to interact with said first retainer upon movement of said stopper to a position proximate said syringe barrel forward end to release said syringe barrel from said first retainer and enable said urging member to move said syringe barrel from said first position to said second position upon release of medicament delivery pressure from said thumb pad.

14. The medical device of claim 13, wherein said hollow shield body further comprises a step having a rear facing surface for receiving one end of said urging member.

15. The medical device of claim 14, wherein said a radial flange receives another end of said urging member.

16. The medical device of claim 15, wherein said step divides said hollow shield body into a first cylindrical portion having a first diameter and a second cylindrical portion having a second diameter different than said first diameter, said urging member being arranged in said second cylindrical portion.

17. The medical device of claim 13, wherein said urging member comprises a spring.

18. A medical device for delivering a medicament to a patient, comprising:
a syringe assembly comprising:
a barrel having a forward end and a rear end and defining a reservoir within in which the medicament may be contained, said barrel having a radial flange arranged between said forward end and said rear end;
a needle cannula having a forward tip and being coupled to said forward end of said barrel and in fluid communication with said reservoir; and
a plunger having a first end with a stopper positioned in said reservoir and a second end having a thumb pad for receiving medicament delivery pressure for causing said plunger to move within said reservoir to cause the medicament to be expelled from said reservoir;
a hollow shield body receiving said syringe barrel therein, said syringe barrel being selectively movable within said shield body between a first position in which said forward tip of said needle cannula is exposed, and a second position in which said forward tip of said needle cannula is contained within said shield body;
a flange clip fixedly coupled to said hollow shield body proximate a rear facing end of said hollow shield body, wherein said flange clip comprises a first retainer fixedly coupled to said hollow shield body to prevent axial movement of said retainer means with respect to said hollow shield body, said first retainer means for releasably securing said syringe barrel in said first position, and second retainer means axially spaced from said first retainer means, said radial flange being held between said first and second retainer means when said syringe barrel is in said second position, said hollow shield body further comprises a rim and said flange clip comprises a recess engaging said rim for connecting said flange clip to said hollow shield body, said recess being arranged axially between said first and second retainers;
means for urging said syringe barrel from said first position toward said second position, said means for urging acting on said radial flange of said syringe barrel; and
said thumb comprising means for interacting with said first retainer upon movement of said stopper to a position proximate said syringe barrel forward end to release said syringe barrel from said first retainer and enable said urging means to move said syringe barrel from said first position to said second position upon release of medicament delivery pressure from said thumb pad.

19. The medical device of claim 18, wherein said means for interacting comprises a configured shape of said thumb pad.

20. The medical device of claim 18, wherein said means for urging comprises a spring.

21. A medical device for delivering a medicament to a patient, comprising:
a reservoir within which the medicament may be contained and having a unitarily molded feature, said reservoir having a forward end to which a needle cannula may be connected;
a plunger receivable in said reservoir and having a thumb pad;
a hollow shield body coupled with said reservoir, said reservoir being selectively movable with respect to said shield body between a first position in which a forward tip of the needle cannula is exposed, and a second position in which a forward tip of the needle cannula is contained within said hollow shield body, said hollow shield body having a flange clip fixedly coupled to said hollow shield body proximate a rear facing end of said hollow shield body, wherein said flange clip comprises a first retainer movable radially outward for engaging said reservoir to enable movement of said reservoir from said first position to said second position and to releasably secure said hollow shield body in said first position, and said flange clip having a second retainer for directly engaging said unitarily molded feature of said reservoir to secure said reservoir relative to said hollow shield body in said second position, said hollow shield body further comprises a rim and said flange clip comprises a recess engaging said rim for connecting said flange clip to said hollow shield body, said recess being arranged axially between said first and second retainers; and said thumb pad being configured to interact with said first retainer upon movement of said plunger in a direction toward said forward end of said reservoir to release said first retainer and enable movement of said reservoir from said first position to said second position.

22. The medical device of claim 21, wherein said second retainer has an inclined front facing surface to allow said unitarily molded feature to pass over said second retainer when said unitarily molded barrel feature is moved from said first position toward said second position.

23. The medical device of claim 21, wherein said first and second retainers comprise flexible arms.

24. The medical device of claim 21, wherein said reservoir comprises a plastic syringe barrel.

* * * * *